(12) United States Patent
Bijalwan et al.

(10) Patent No.: US 12,112,478 B2
(45) Date of Patent: Oct. 8, 2024

(54) METHOD AND SYSTEMS FOR PREDICTING MEDICAL CONDITIONS AND FORECASTING RATE OF INFECTION OF MEDICAL CONDITIONS VIA ARTIFICIAL INTELLIDENCE MODELS USING GRAPH STREAM PROCESSORS

(71) Applicant: Blaize, Inc., El Dorado Hills, CA (US)

(72) Inventors: Deepak Chandra Bijalwan, Hyderabad (IN); Dinakar C. Munagala, El Dorado Hills, CA (US)

(73) Assignee: Blaize, Inc., El Dorado Hills, CA (US)

( * ) Notice: Subject to any disclaimer, the term of this patent is extended or adjusted under 35 U.S.C. 154(b) by 0 days.

(21) Appl. No.: 18/544,662

(22) Filed: Dec. 19, 2023

(65) Prior Publication Data

US 2024/0119596 A1    Apr. 11, 2024

Related U.S. Application Data

(62) Division of application No. 17/238,289, filed on Apr. 23, 2021, now Pat. No. 11,908,132.

(51) Int. Cl.
*G06K 9/00*    (2022.01)
*G06F 18/21*    (2023.01)
(Continued)

(52) U.S. Cl.
CPC .......... *G06T 7/0012* (2013.01); *G06F 18/214* (2023.01); *G06F 18/2163* (2023.01);
(Continued)

(58) Field of Classification Search
CPC .................. G06T 7/0012; G06T 5/002; G06T 2207/10116; G06T 2207/20081;
(Continued)

(56) References Cited

U.S. PATENT DOCUMENTS 10,834,142 B2    11/2020 Bhatia et al.
10,834,221 B2    11/2020 Tong et al.
(Continued)

FOREIGN PATENT DOCUMENTS

CN    110348515 A    *    10/2019
CN    110490880 A    *    11/2019
(Continued)

*Primary Examiner* — Xin Jia
(74) *Attorney, Agent, or Firm* — Brian R. Short (57) ABSTRACT

Systems and methods are disclosed for predicting one or more medical conditions utilizing digital images and employing artificial intelligent algorithms. The system offers accurate predictions utilizing quantized pre-trained deep learning model. The pre-trained deep learning model is trained on data samples and later refined as the system processes more digital images or new medical conditions are incorporated. One pre-trained deep learning model is used to predict the probability of one or more medical conditions and identify locations in the digital image effected by the one or more medical conditions. Further, one pre-trained deep learning model utilizing additional data and plurality of digital images, forecasts rate of infection and spread of the medical condition over time.

20 Claims, 7 Drawing Sheets

Related U.S. Application Data (60) Provisional application No. 63/019,279, filed on May 2, 2020.

(51) Int. Cl.

| | |
|---|---|
| *G06F 18/214* | (2023.01) |
| *G06N 3/08* | (2023.01) |
| *G06T 5/70* | (2024.01) |
| *G06T 7/00* | (2017.01) |
| *G06V 10/774* | (2022.01) |
| *G06V 10/776* | (2022.01) |
| *G06V 10/82* | (2022.01) |
| *G16H 30/40* | (2018.01) |
| *G16H 50/20* | (2018.01) |

(52) U.S. Cl.
CPC .............. *G06F 18/217* (2023.01); *G06N 3/08* (2013.01); *G06T 5/70* (2024.01); *G06V 10/774* (2022.01); *G06V 10/776* (2022.01); *G06V 10/82* (2022.01); *G16H 30/40* (2018.01); *G16H 50/20* (2018.01); *G06T 2207/10116* (2013.01); *G06T 2207/20081* (2013.01); *G06T 2207/20084* (2013.01)

(58) Field of Classification Search
CPC . G06T 2207/20084; G06T 2207/10081; G06T 2207/30061; G06F 18/214; G06F 18/2163; G06F 18/217; G06N 3/08; G06N 3/045; G06V 10/774; G06V 10/776; G06V 10/82; G06V 2201/03; G16H 30/40; G16H 50/20; G16H 50/70; G16H 50/80
See application file for complete search history.

(56) References Cited

U.S. PATENT DOCUMENTS

| | | | |
|---|---|---|---|
| 10,848,709 B2 | 11/2020 | Zhang et al. | |
| 10,866,985 B2 | 12/2020 | Chandra Sekar Rao et al. | |
| 2019/0110020 A1 | 4/2019 | Zhang et al. | |
| 2020/0202527 A1* | 6/2020 | Choi | G06T 5/73 |

FOREIGN PATENT DOCUMENTS

| | | | | |
|---|---|---|---|---|
| WO | WO2019240257 A1 | 12/2019 | | |
| WO | WO-2020102914 A1 * | 5/2020 | ........... | G06T 7/0012 |
| WO | WO-2020183799 A1 * | 9/2020 | ............... | G06T 5/70 |

\* cited by examiner

| Infection Score | | |
|---|---|---|
| Stage 1 | Early Stage | 0-4 Days |
| Stage 2 | Progressive Stage | 5-8 Days |
| Stage 3 | Peak Stage | 10-13 Days |
| Stage 4 | Absorption Stage | >14 days |

| Initial Prediction | |
|---|---|
| Medical Condition | Probability |
| Flu | 10% |
| Covid-19 | 50% |
| Pneumonia | 30% |
| Healthy | 10% |

Figure 6C

| Classification of Medical Condition | |
|---|---|
| Medical Condition | Probability |
| Flu | 0% |
| Covid-19 | 90% |
| Pneumonia | 10% |
| Healthy | 0% |

METHOD AND SYSTEMS FOR PREDICTING MEDICAL CONDITIONS AND FORECASTING RATE OF INFECTION OF MEDICAL CONDITIONS VIA ARTIFICIAL INTELLIDENCE MODELS USING GRAPH STREAM PROCESSORS

RELATED APPLICATIONS

This patent application is a divisional patent application of U.S. patent application Ser. No. 17/238,289, filed Apr. 23, 2021, which claims priority to provisional patent application 63/019,279, filed May 2, 2020 which are all herein incorporated by reference.

FIELD OF EMBODIMENTS

The described embodiments relate generally to predictions of medical conditions. More particularly, the described embodiments relate to Artificial Intelligence (AI) systems and methods for classifying, identifying locations effected by medical condition, and forecasting medical conditions.

BACKGROUND

In a situation where a large population needs testing and diagnoses in a short amount of time, lot of medical resources, trained staff and experts in data management are required. Detecting the presence of a virus in an individual by examining the nasal swab or other means and processing the results for a population is an enormous task involving trained medical personnel and support staff. Traditional process of screening the population, notifying and suggesting infection control is time consuming. Comparing against previous data of patients is compute power intensive, hence need dedicated or powerful systems. Such systems may be expensive and immobile.

There is a need for automated systems and methods for accurate, timely detection, quick decision making, less compute intensive systems and requiring fewer medical experts to deploy in the field.

SUMMARY

Method for processing data such as a digital image of at least portion of a user for predicting one or more medical conditions. The method comprises of pre-processing the digital image by removing noise, aligning, and correcting luminance of the digital image, generating an initial prediction, wherein the initial prediction comprises a probability of one or more medical conditions by processing the pre-processed image through one pre-trained deep learning model. Predicting an output based on the initial prediction, where in the predicting includes, modifying the probability of the one or more medical conditions by labelling the preprocessed image from the one or more medical conditions and computing the probability of the one or more medical conditions; and identifying at least a location in the digital image effected by the one or more medical conditions, wherein the identifying includes generating a plurality of anchor boxes and estimating at least one final anchor box.

In some embodiment, predicting can include forecasting a rate of spread of the one or more medical conditions and spread of the one or more medical conditions over time based on additional medical data when a plurality of digital images over a period of time are available.

First step in generating the pre-trained deep learning model comprises generating a floating-point model utilizing a plurality of data samples and compacting the floating-point model. In some embodiments, quantization techniques are applied on floating-point model to output a mixed precision quantized model.

In some embodiments, the predicted output is compared with the digital image by an expert user. The digital image is added to the data samples for updating the model when the predicted output is incorrect.

In some embodiments, the digital image type comprises any one of X-Ray, CT-Scan, and non-medical image. In some embodiments, X-Ray images are used for generating the initial prediction while other types of images are discarded. In an example, the one or more medical conditions is Covid-19. In some embodiments, the plurality of data samples comprises positive data samples and negative data samples, wherein the positive data samples comprise X-Ray samples and negative samples comprises other types. Only positive data samples are used for generating the model. The positive samples are labelled with a medical condition, images are aligned. The data samples are balanced such that similar number of samples are exists across different medical conditions.

In an embodiment, the balanced data samples are divided into training data samples for generating the pre-trained deep learning model, test data samples for testing the pre-trained deep learning model and validation data samples for validation of the pre-trained deep learning model. In some examples, the pre-trained deep learning model is validated by processing the validation data samples through the pre-trained deep learning model and comparing the predicted output with the labelled medical condition. Similarly, test data samples are used for testing system randomness.

In an embodiment, generating the pre-trained deep learning model includes pre-processing the plurality of training data samples to reduce noise, adjust illumination and image alignment to generate pre-processed training data samples, extracting textural features from the pre-processed training data samples, generating a map of the textual features, and processing through a decision network to train the pre-trained deep learning model to the predict the output.

In an embodiment, when new data samples are received or when the model needs to be trained for a new medical condition, the floating-point model is updated utilizing the new data samples and data samples from the new medical condition, later distilled and quantized to update the model.

In an embodiment, a graph stream processing system, comprises of an inference module operative to execute instructions on a plurality of graph streaming processors (GSP) to process a digital image associated with a patient, generating an initial prediction utilizing pre-trained weights in a mixed precision pre-trained deep learning model; and a post-processing module operative to execute instructions on the GSP to compute a probability of a medical condition of the patient based on the initial prediction and identify a location of the medical condition based on the initial prediction and forecast a rate of spread of the medical condition and spread of the medical condition over time based on a plurality of digital images, the initial prediction and additional medical data.

In an embodiment, a data processing method comprises, receiving a digital description of at least a symptom of a medical condition in a first format; performing, using a plurality of GSP, an (AI based) initial prediction of the medical condition by processing the digital description through a pre-trained deep learning model to generate a probability of the medical condition; determining using the plurality of GSP, adjusting the probability of the medical condition, identifying a location in the description of the medical condition, and forecasting a rate of spread of the medical condition and a spread of the medical condition over time based on a plurality of digital descriptions and additional medical data. In an embodiment the first format comprises X-ray and the medical condition is Covid-19.

DETAILED DESCRIPTION

Figure 1:
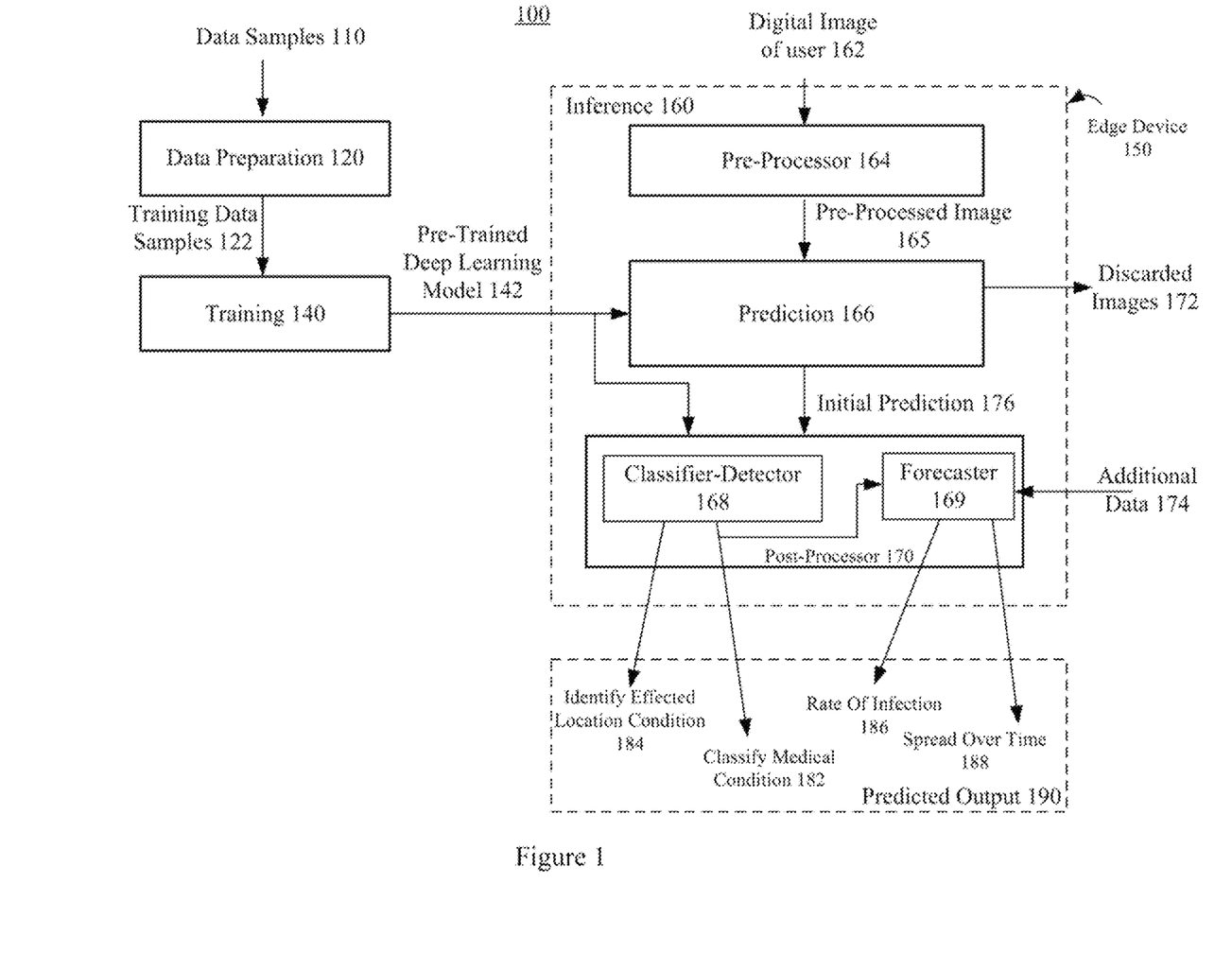
FIG. 1 shows a block diagram of system for detecting medical conditions utilizing a pre-trained deep learning model.

FIG. 1 is a schematic diagram illustrating an example of an Artificial intelligence (AI) system 100 for predicting one or more medical conditions utilizing a pre-trained deep learning model.

AI System 100 comprises of Data Preparation 120, Training 140, Inference 160. System 100 utilizes pre-trained deep learning model 142 to classify, detect and forecast one or more medical conditions. In the described embodiments, medical condition or target medical condition includes all diseases, lesions, disorders, or non-pathologic condition that normally receives medical treatment. A few examples of medical condition among others are flu, Covid-19, and pneumonia.

Artificial Intelligence (AI) can be an effective tool in identifying early infections and medical conditions. Unlike normal circumstances, in a pandemic situation where a large population needs testing and diagnoses, AI can be extremely useful. AI can be utilized in monitoring the conditions of the infected patients using fewer medical experts. Improvement in treatment consistency and decision making can be seen by developing useful algorithms. X-ray is one of the means for diagnosing Covid-19. AI can be helpful in the diagnosis and treatment of Covid-19 infected patients. Inference 160 can be executed on an edge device 150 comprising of Graph Stream Processors. Deep learning pre-trained model 142 is a mixed precision quantized model with a small footprint is generated on any computing device and transmitted to an edge device 150 for processing. Edge device 150 in some embodiments can be a GSP system.

GSP systems are ideal for processing instructions on different data sets. Digital image of user 162 is processed efficiently by graph streaming processors as the tasks of processing image can be run in parallel threads. Hardware built scheduler is very efficient in scheduling the threads for operation in the graph streaming processor array. GSP systems consume less power, small in size and have large compute power, hence they can be deployed in the field for detection of medical conditions. Automated analysis systems running on GSP systems employing deep learning AI algorithms aid in the diagnosis of Covid-19.

In an embodiment, System 100 can detect abnormalities and extract textural features of the altered lung parenchyma that could be related to specific signatures of the Covid-19 virus using Cross Validation (CV) and Deep Learning networks. System 100 combines AI with radiomics in a novel analysis tool designed to identify disease and its progression. AI systems can be used to track and forecast the nature of the progression of the disease about the risks of the infection and its likely spread from the available data System 100 is a low power; automated system enabling customers/hospital/medical research lab/doctors/radiologist/patient to accelerate the diagnostic process and analyze the x-rays in a very short time without expert knowledge/help. Normal chest x-ray/CT scan images are converted to digital images using camera or scanners, then pre-processed to remove noise and processed through GSP system to predict the probability of symptoms and identify the type of medical condition using the deep learning classifier/detector. It is contemplated that in some embodiments, digital description of a medical condition can be used instead of a digital image. The efficiency, lower consumption and accuracy of the system would not be any different due to processing of digital description.

Inference 160 receives digital image of a user 162 who is suspected of having one or more symptoms of one or more medical conditions. In an example, the digital image is a chest x-ray of a user suspected of Covid-19 symptoms. Inference 160 processes the digital image utilizing pre-trained deep learning model 142, classifies the probability of the digital image of the user into one or more medical conditions 182, detects i.e. identifies effected locations in the digital image, forecasts rate of infection and spread over time. System 100 generates multiple outputs, i.e. predicted output 190 based on one pre-trained deep learning model 142. In some embodiment, the predicted output 190 is stored on edge device 190 or stored in a database in cloud or communicated to user via email or display. Inference 160 can be executed on any system, however a GSP system offers benefit of size, and fast computation due to fixed point processing.

Pre-processor 164 receives a digital image of user 162 of relevant portion of the body. In an embodiment, digital image is a medical image of user of a relevant portion of the body. The digital medical image can be x-ray, CT scan or any other type of medical image. Pre-processor 164 removes noise, aligns, and corrects for luminance of the digital image 162 and generates a pre-processed image 165. Prediction 166 utilizes pre-trained weights in the deep learning model 142 to generate an initial prediction 176 based on the pre-processed digital image 165. The pre-trained deep learning model is trained to predict the probability of one or more medical conditions. Pre-trained deep learning model 142 is generated using a set of data samples. In response to earlier predictions and new data samples system 100 updates model 142. The updated model is transmitted to edge device 150 by any means communication means over the internet or memory storage devices. The ability to change and adapt based on new data samples and new medical conditions enables the system to adapt to variations in the environment, mutating strains of viruses as well as adapt to new medical conditions. Data samples of one or more known medical conditions are used for training the model 142. In the described embodiments pre-trained deep learning model 142 and model 142 are used synonymously. Data samples 110 are first processed to label medical conditions and prepare training data samples 122. Training 140 comprises of generating model 142, learning and later refining the model, and updating the model when new medical conditions are added to the system. Training 140 processes the training data samples 122 to extract features of the one or more medical conditions from the digital image and classifies the extracted features as related to a medical condition.

Training 140 is a multistage model, a combination of multiple networks with the concept of meta-learning using stacking technique. Residual neural network is used as a base backbone network to extract features from images and build a fine feature map for further processing. Data learning models generally require large set of data for training. The quality of the AI system depends on the data samples that is available for training. The data set is augmented and balanced, and training parameters are adjusted based on verification 370, validation 390 and test 392 described related to FIG. 3.

Prediction 166 processes the pre-processed digital image utilizing pre-trained weights in the deep learning model 142 and outputs an initial prediction 176. Initial prediction 176 comprises of an initial probability of each of the medical conditions or classes the pre-trained deep learning model 142 is trained on. For example, an initial prediction 176 could be that the user has Covid-19 with 50% probability, pneumonia with 30% probability, flu with a 10% probability and 10% probability that the user is healthy at risk. In an embodiment, prediction 166 processes only x-ray images, non-x-ray images 172 are discarded before generating initial prediction 176. In other embodiments, all digital images are processed.

Post Processor 170, utilizing the pre-trained deep learning model 142 and the initial prediction predicts output 190. In some embodiment, the predicted output is stored is a database or on edge device or communicated to user via a display on edge device 150 or printed or emailed to user or communicated to user in other formats. Classifier-detector 168 comprises of a classifier pre-trained model and a detector pre-trained model. The classifier employs deep learning techniques such as SoftMax to label the input image from the list of target medical conditions and arrive at an enhanced probability of the medical conditions associated with the digital image of user 182. For example, a predicted output 190 comprising of classify medical condition 182 could be that the received digital image of user 162 has Covid-19 with 90% probability, pneumonia with 5% probability, flu with 5% and the overall impression is that the user is affected by Covid-19.

Detector model applies deep learning techniques such as Anchor Boxes producing multiple anchor boxes wherein an anchor box is a region in the digital image 162. Detector model samples a plurality of regions in the digital image 162 and determines whether any of the plurality of regions contain objects of interest. Additionally, detector model adjusts the boundaries of the regions to predict the final anchor box accurately.

Detector model also utilizes Non-Maximum Suppression (NMS) to estimates the final anchor box which is a location of the effected region by the medical condition. An example of location identification is upper right lung due to Covid-19.

Additional data 174 along with the initial prediction 176, pre-trained model 142 and output of classifier 182 enables forecaster 169 to predict rate of infection 186 and spread of the medical condition over time 188. Additional data 174 such travel history, location of residence, gender, age, and other symptoms relevant the medical condition is input into the system. In an example, for Covid-19, symptoms such as fever, cough, throat pain, expectoration, chills, fatigue, and chest pain could be useful information in forecasting.

Utilizing the plurality of images received at different intervals, forecaster 169 tracks the changes in the features along with additional data 174 to reduce the false negatives. Forecaster 169 analyzes the abnormalities in the digital image received at different intervals and assigns the progression of the medical condition. In an example, the day of initial symptom is considered as day 0. Forecaster 169 tracks and predicts rate of infection based on temporal changes to the digital images along with additional data 174.

Figure 6A:
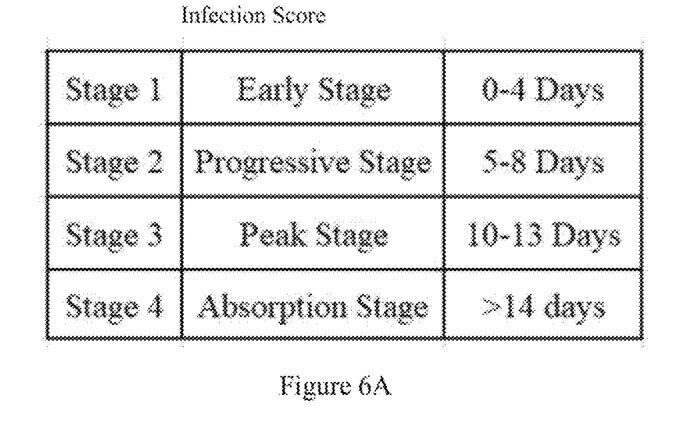
FIG. 6A shows an example infection score.
Figure 6B:
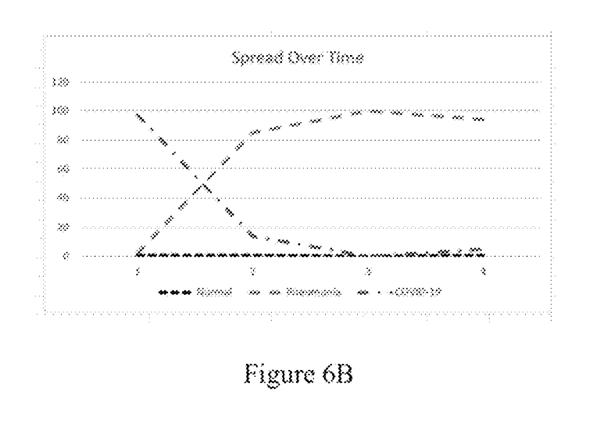
FIG. 6B shows an example spread of the medical condition over time.
Figure 6C:
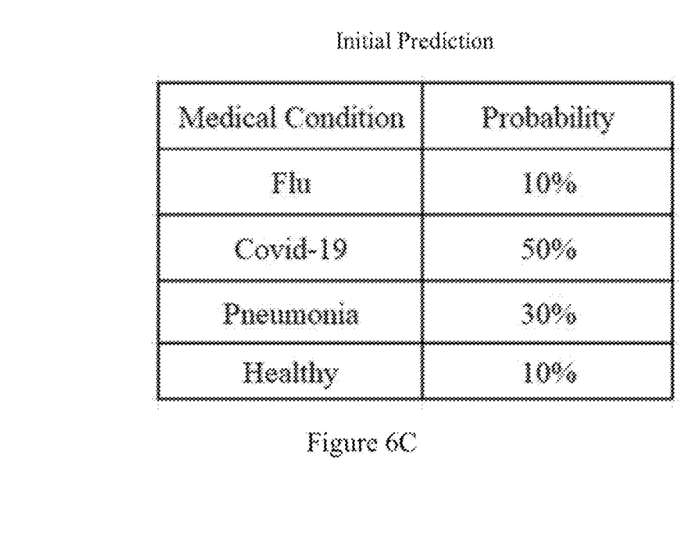
FIG. 6C is an example initial prediction.

Forecaster 169 analyzes plurality of images received at different intervals and assigns an infection score. Forecaster 169 further computes a stage score median and standard deviation. External factors such as patient age, health conditions which are received from additional data 174 are combined with stage median and deviation scores to predict rate of infection and disease progression. Example Infection score is shown in FIG. 6A Comparing digital images of user 162 with previous images helps identifying spread over time 188 which is the progression of the medical condition or recovery from the medical condition. FIG. 6B is an example of the spread over time where y-axis is a probability of medical condition and x-axis indicates the days of the samples FIG. 2 describes a method 200 of predicting a medical condition utilizing digital images of users and a pre-trained deep learning model. Method 200 in some embodiments can be executed on a GSP system. Method 200 comprises of receiving a digital image of a user 162. Pre-processing digital image 104 prepares the digital image by removing noise from the image, aligning image so that algorithms can be applied, and adjusting the brightness so that features are visible. System 200 utilizes one pre-trained deep model and the pre-processed image to classify and detect medical conditions. System 200 utilizes one pre-trained deep model, the pre-processed image, and additional data to forecast rate of infection and spread over time. Pre-trained deep learning model 142 is applied on the pre-processed image 104 in prediction 166. An initial prediction of the medical condition generated by prediction 166 comprises of an initial probability of the one or more medical conditions the pre-trained deep learning model 142 is trained on. An example of the initial prediction is shown in FIG. 6C.

Figure 2:
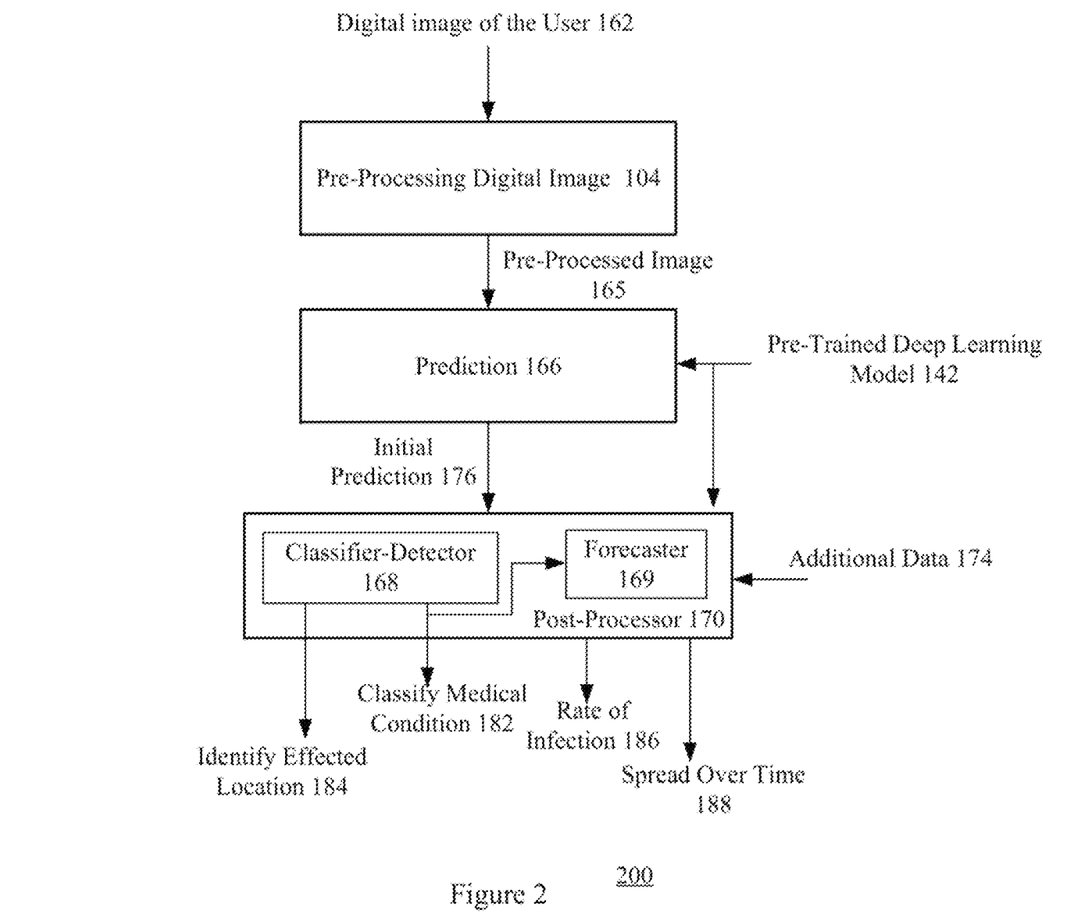
FIG. 2 shows a method of detecting a medical condition.
Figure 6D:
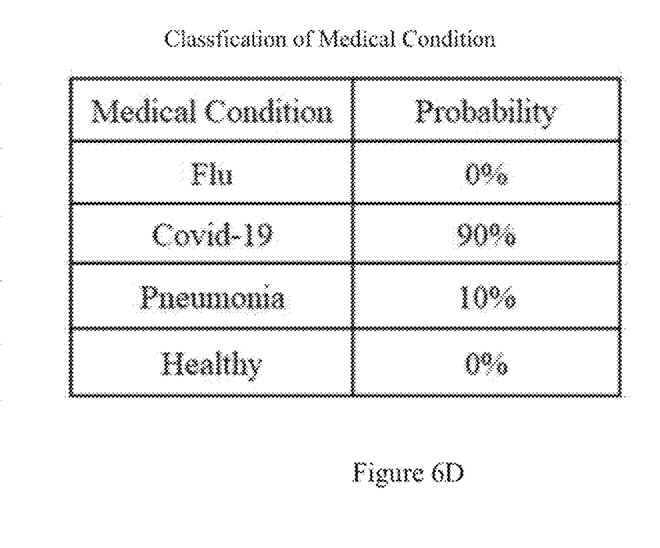
FIG. 6D is an example of classification of a medical condition.
Figure 6E:
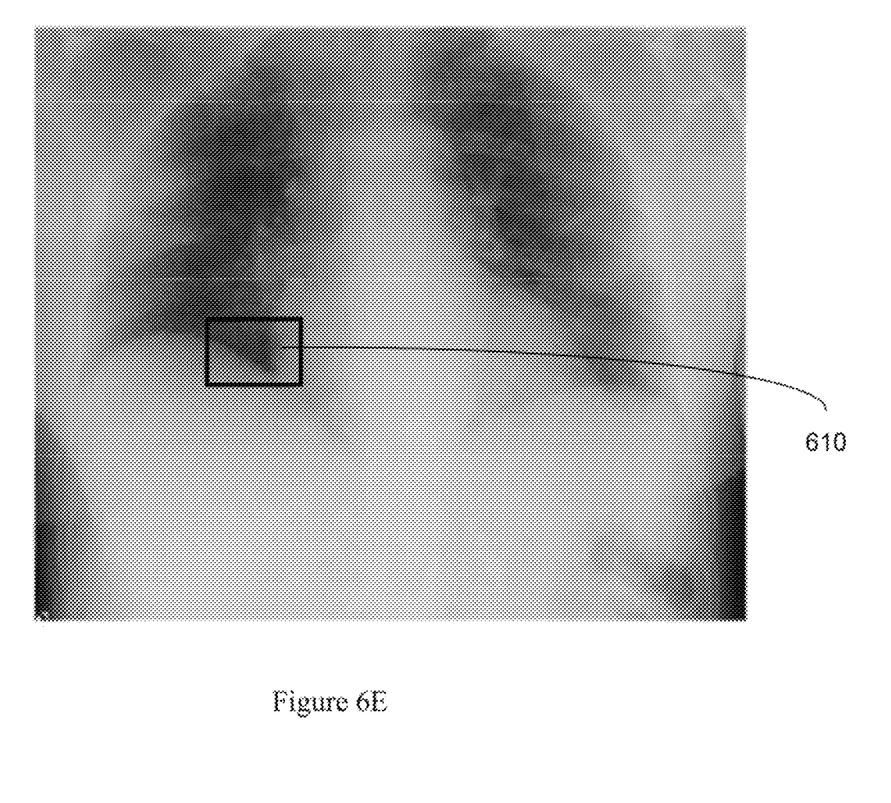
FIG. 6E is an example of detection of a medical condition.

Post-processor 170 comprises of classifier-detector and forecaster. Classifier-detector applies deep learning techniques such as SoftMax and Non-Maximum Suppression (NMS) to estimate the probability of the medical conditions and localize the affected region. Classify medical condition 182 comprises of a probability of each of the medical conditions the pre-trained deep learning model 142 is trained on. FIG. 6D shows an example classification of medical condition Post-Processor 170 further applies deep learning techniques such as Anchor Boxes to identify effected location of the digital image 184 due to the medical conditions trained. The classified images are processed through classifier-detector 168 to associate a location effected by the medical condition with a feature in the image. Multiple anchor boxes are produced from detector by deep learning techniques such as Anchor Boxes. Detector utilizes Non-Maximum Suppression to estimate the final anchor box which is a location of the effected box by the target medical condition. An example output of detector is shown in FIG. 6E. 610 points to a location in the digital image of user 162 affected by the target medical condition.

Additional data 174 along with the initial prediction enable forecasting of rate of infection 186 and spread of the medical condition over time 188. Additional data 174 such as travel history, location of residence, gender, age, and other symptoms based on the medical condition is input into the system. In an example, for Covid-19, symptoms such as fever, cough, throat pain, expectoration, chills, fatigue, and chest pain could be useful information in forecasting. Digital images 162 received at different intervals of time are used to project spread of the medical condition over time.

Rate of infection 186 compares the digital images of user 162 with previous images at different times to show increase in progress of the medical condition compared to previous image.

Comparing digital images of user 162 with previous images at different times helps identifying spread over time 188 which is the progression of the medical condition or recovery from the medical condition.

Figure 3:
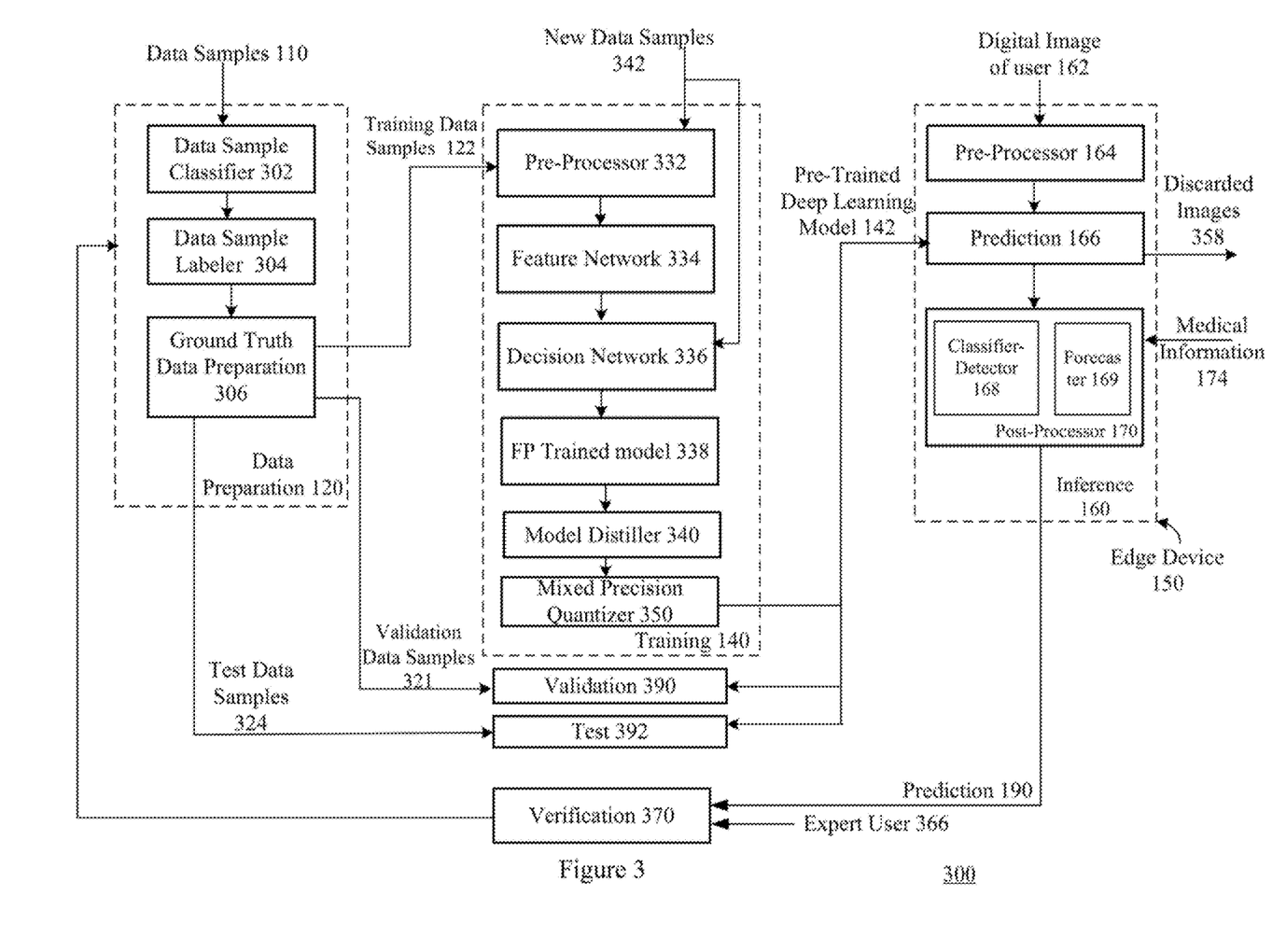
FIG. 3 shows a system block diagram of generating pre-trained deep learning model and prediction of medical conditions.

In an embodiment FIG. 3 depicts an AI system 300 for predicting one or more medical conditions where optimized pre-trained deep learning model is ported for execution on a target hardware such as GSP system. The system comprises of capturing chest x-ray/CT scan in a digital image format. The image is pre-processed to remove noise and the AI model processes the digital image on a GSP system to predict the probability of symptoms and identify the type of medical condition using a deep learning classifier-detector with a good accuracy. Optionally, the system can receive additional medical conditions to improve the accuracy of the prediction. Since the digital images are processed on a GSP, the throughput of system is high as the GSP system can process fast.

FIG. 3 is system of prediction medical conditions by an AI system. System 300 generates pre-trained deep learning model 142 utilizing data samples 110. The output of the AI system 300 depends on the quality of the pre-trained model 142. Developing a trained model requires large number of historical data from the domain that is used as training data. Labelling the data samples and processing the samples is compute intensive. Pre-trained deep learning model is developed and later fine-tuned as data samples vary or new examples not seen by the model during training are added to the system. Data Preparation 120, Training 140 require compute power and memory, hence executed on compute intensive systems.

In a non-limiting embodiment, AI system 300 receives data samples 110. Data samples 110 are digital images related to a first medical condition. Digital images can be any of the of medical imaging technologies like X-Ray, Computed tomography (CT), Magnetic resonance imaging (MRI) scan of human body parts. Data sample classifier 302 classifies data samples 110 into positive and negative samples. In an embodiment, positive data samples are X-Ray samples and negative data samples are other than X-Ray samples. Other embodiments could include more than one type of digital image. The positive data samples are labeled as related to the one or more medical conditions, or normal condition by data sample labeler 304. In an example the data samples 110 are labelled as healthy, flu, pneumonia, and Covid-19.

Ground truth data preparation 306 comprises of preparing the image samples for training. The negative data samples and the labeled positive data samples are used for ground truth data preparation 306 where images are rotated, aligned, and cleaned. Next step in data preparation comprises of data balancing. Data balancing is the technique of having data samples of different classes or medical conditions which mimic the system outcome which in turn improves the accuracy of the model. One example of data balancing could be to have about 10% of x-ray samples with Covid-19, 10% x-ray samples with pneumonia, 60% x-ray samples with no infection, 10% flu, and 10% non-x-ray type reflecting the current system output. The percentage of various classes can be adjusted when the operating system environment changes. Balanced data is then divided into training data samples 320, validation data samples 321 and test data samples 324. Training data samples 320 are used for training model 142. Validation data samples 321 and test data samples 324 are held back from training the model. System 300 can be tuned to alter the percentage of samples for training, validation and test based on the quality of trained model. In an embodiment, the samples can be divided into 80% for training, 10% for validation and 10% for test.

Figure 4:
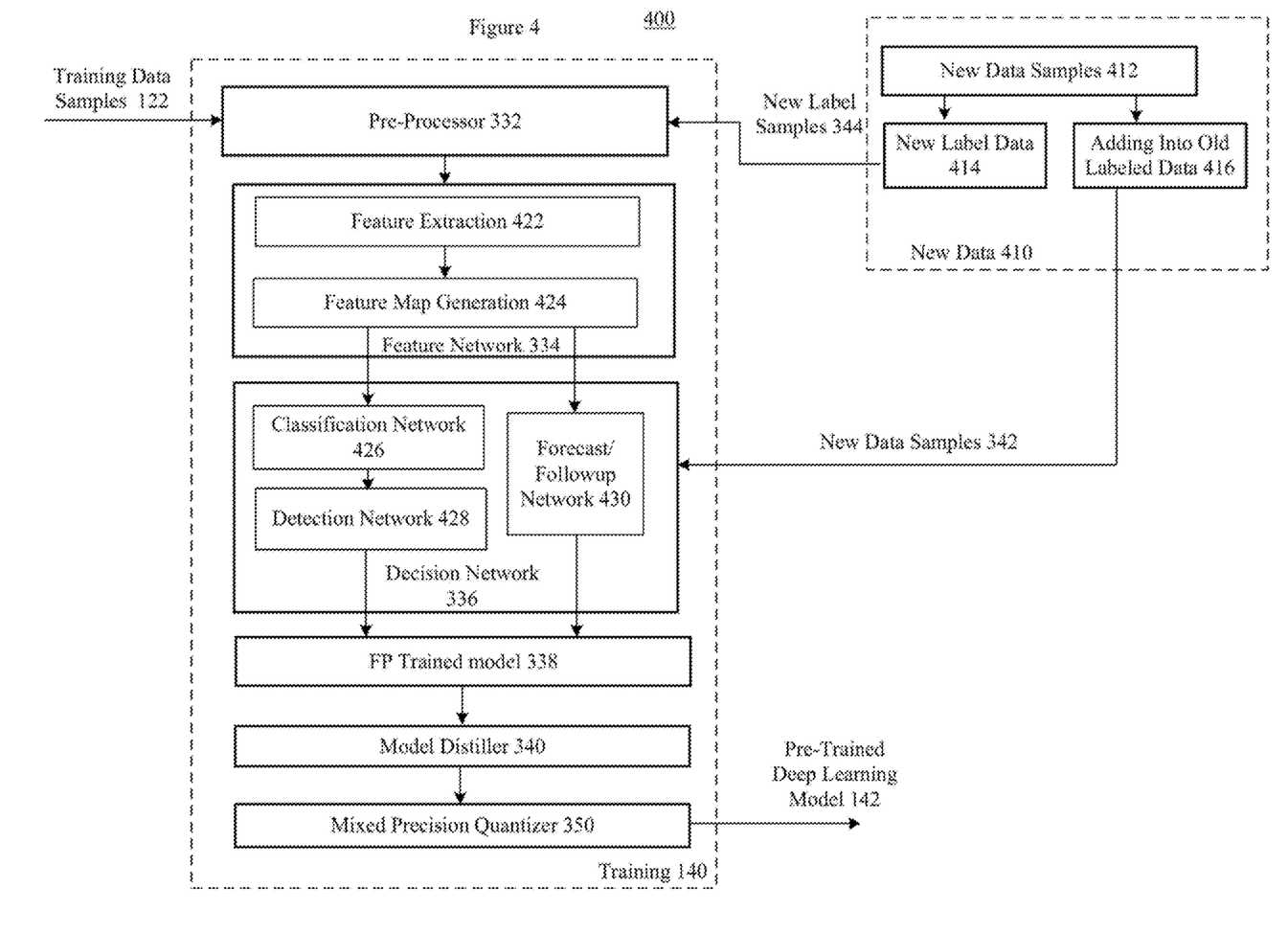
FIG. 4 shows a method of generating a pre-trained deep learning model.

In an embodiment training 140 generates a pre-trained deep learning model 142 utilizing training data samples 122. FIG. 4 explains the details of the model generation. The computation critical stage is inference 160 is executed on small devices and executed whenever new image is acquired. Inference 160 is executed on any efficient system. GSP system offers low power and compact size which is ideal for mobile system or geographically remote systems. GSP systems are very efficient in processing fixed-point models. Pre-trained deep learning model is tuned to operate most efficiently on GSP systems by model distiller 340.

Digital image of user 162 who needs a diagnosis of one or more medical conditions is received by pre-processor 164. The digital image is pre-processed to remove noise, aligned as per system requirements, and corrected for luminance Prediction 166 processes the pre-processed digital image utilizing pre-trained deep learning model 142 and outputs an initial prediction. Initial prediction comprises of an initial probability of each of the medical conditions or classes model 142 is trained on. For example, an initial prediction could be that the received digital image of user 351 has Covid-19 with 50% probability, pneumonia with 30% probability, flu with a 10% probability and 10% probability that the user is healthy. Prediction 166 processes only x-ray images, non-x-ray images 358 are discarded before generating initial prediction 176.

Post-processor 170, utilizing the pre-trained deep learning model 142 and the initial prediction computes predicted output 190. Classifier-detector 168 classifies a medical condition of the user 182 with a higher accurate probability. Deep learning techniques such as Non-Maximum Suppression (NMS) and SoftMax is applied to arrive at an enhanced probability of the medical conditions. For example, a predicted output 190 could be that the received digital image of user 162 has Covid-19 with 90% probability, pneumonia with 5% probability, flu with 5% and 0% probability that the user is healthy. Classifier-detector 168 applies deep learning techniques such as Anchor Boxes to identify effected location of the digital image 184 due to the medical condition. An example of location identification can be upper right lung due to Covid-19.

Additional data 174 along with the initial prediction 176, trained model enable forecaster 169 to predict rate of infection 186 and spread of the medical condition over time 188. Additional data 174 such travel history, location of residence, gender, age, and other symptoms based on the medical condition is input into the system. In an example, for Covid-19, symptoms such as fever, cough, throat pain, expectoration, chills, fatigue, and chest pain could be useful information in forecasting. Plurality of digital images of user 162 received at different intervals of time are used to project spread of the medical condition over time. In some embodiments, predicted output is displayed. In an example display classify medical condition 182 and identify effected location is displayed in text, where as rate of infection 186 and spread over time 188 are displayed in graphical format.

Comparing digital images of user 162 with previous images helps identifying spread over time 188 which is the progression of the medical condition or recovery from the medical condition.

To verify the operation of the system, a certain percentage of prediction 190 is verified manually by an expert user 366 in verification 370. In some embodiments, expert user can be a medically trained doctor. This step is performed by comparing the digital image of user 162 with predicted output 190 by expert user 366. Images that failed verification are added to the data sampler 304 which in turn is used to update model 142. The feedback helps in improving the pre-trained deep learning model 142.

Pre-trained data model 142 is evaluated on validation data samples 321. Validation 390 gives an estimate of the quality of the model. Validation can help in tuning certain training parameters. Validation data samples 321 are held back from training the model. Similarly, model 142 is evaluation on test data samples 324 in test 392. Test data samples are curated to span various classes and other parameters. Test data samples are generally held back from training the model. Test data 124 used to test system or model randomness. Training model is updated periodically depending on the verification and validation results.

FIG. 4 is method 400 of generation a pre-trained deep learning model 142. The first step in the process of generating the model 142 is pre-processor 332. Pre-processor 332 removes noise, aligns, and corrects for luminance of the training data samples 122. Training data samples 122 are further processed in feature network 334. Feature extraction 422 identifies various features present in the training data samples 122. In some embodiments, feature extraction 422 reduces the size of the image while still representing interesting portions of the image. Feature map generation 424 processes the features extracted image where the tensor holds the feature values.

Decision network 336 enables one model 142 output multiple outputs by teaching the model 142 to classify a medical condition, identify effected location and forecast. Decision network 336 comprises of classification network 426, detection network 428 and forecast/follow-up network 430. Classification network 426 employs deep learning techniques such as SoftMax to processes the output of feature map generation 424 in order to learn the different features associated with medical conditions there by co-relating one or more image features with different class/label/medical conditions. This step requires large computation. Since this step is performed occasionally, the system performance is not impacted. The classified images are processed through detection network 428 to associate a location effected by the medical condition with a feature in the image. Multiple anchor boxes are produced from detection network 428 by deep learning techniques such as Anchor Boxes. Detection network utilizes Non-Maximum Suppression (NMS) to estimate the final anchor box which is a location of the effected box by the target medical condition.

Forecast/Follow up network 430 receives output of feature map generation 424, classification network 426 generates a prediction model. The prediction model is generated to predict rate of infection 186 and spread of the medical condition over time 188. Additional data such travel history, location of residence, gender, age, and other symptoms relevant the medical condition is input into the system. In an example, for Covid-19, symptoms such as fever, cough, throat pain, expectoration, chills, fatigue, and chest pain could be useful information in forecasting.

Utilizing the plurality of images received at different intervals, the prediction model tracks the changes in the features along with additional data 174 to reduce the false negatives. The prediction model analyzes the abnormalities in the digital image received at different intervals and assigns the progression of the medical condition.

The prediction model analyzes plurality of images received at different intervals and assigns an infection score and further computes a stage score median and standard deviation. External factors such as patient age, health conditions are combined with stage median and deviation scores to predict rate of infection and disease progression.

Method 400 generates a FP trained model 338 by fusing data from detection network 428 and forecast/follow-up 430. Trained model 338 is a floating-point model comprising of pre-trained weights and bias of all layers of training 140. In some embodiments the FP trained model is a 32-byte floating point model. Systems executing floating point model requires extensive computing power and memory as the model is large. To reduce the system requirements model distiller 340 reduces the size of FP trained model 338 to a smaller model while retaining the knowledge in the model. Model distiller 340 reduces the memory requirement by downgrading the datatype. Breadth of the pre-trained model 142 is reduced by reducing the number of features. While the depth of the trained mode 142 is reduced by reducing layers of the trained model Mixed precision Quantizer 350 further applies quantizing techniques on the distilled model to change the floating-point model into a small data type number. To retain the accuracy of the trained model and reduce the bandwidth a combination of layer weights, feature, and feature values are processed and experimented with different data types to arrive an optimal data type precision Quantizing during training is an effective method of retaining high accuracy. Distillation and quantization dramatically reduce both the memory requirements and computational cost requirements. Training 140 is generally executed on a system with large computational power. The size of the model and number of computations is not as important as model is trained rarely. Quantizer generates a mixed precision quantized model 142. In some embodiments model 142 is an 8-byte model. In an example, the steps of distillation and quantizer reduce the size of the memory footprint by 4 times while reducing the accuracy by a small percentage. These steps help in optimizing the model 142 to run smaller systems such as a GSP system. Model 142 is computed on any computing device and transferred to edge device 150 for executed on digital images for prediction.

Model 142 can be trained to address changes in data samples, predict new medical conditions or mutation of a virus. To incorporate new medical conditions into method 400, new data samples 342 is added to training 140.

To train the model with new target medical condition or new data samples, the system receives new data samples 412. New data samples 412 are first labeled as new target medical condition samples in new label data 414 and existing medical condition samples, adding into old labeled data 416.

Data samples of new target medical condition, new label samples 344 are pre-processed is pre-processor 332, feature extraction 422 and feature map generation 424. Model 142 is re-trained with new data samples 342 which includes data samples new data samples of exiting labels or medical conditions. New label samples 344 and New data samples 342 are processed through decision network 336. FP trained model 338 is updated to include the new medical condition or updated with new data samples. Finally, model distiller processes the new FP trained model 338 to update model 142 to include the new medical condition. Updated model 142 is stored on any device computing training 140 and transmitted to one or more edge devices 150 deployed in the field to detect/predict one or more medical conditions.

Figure 5:
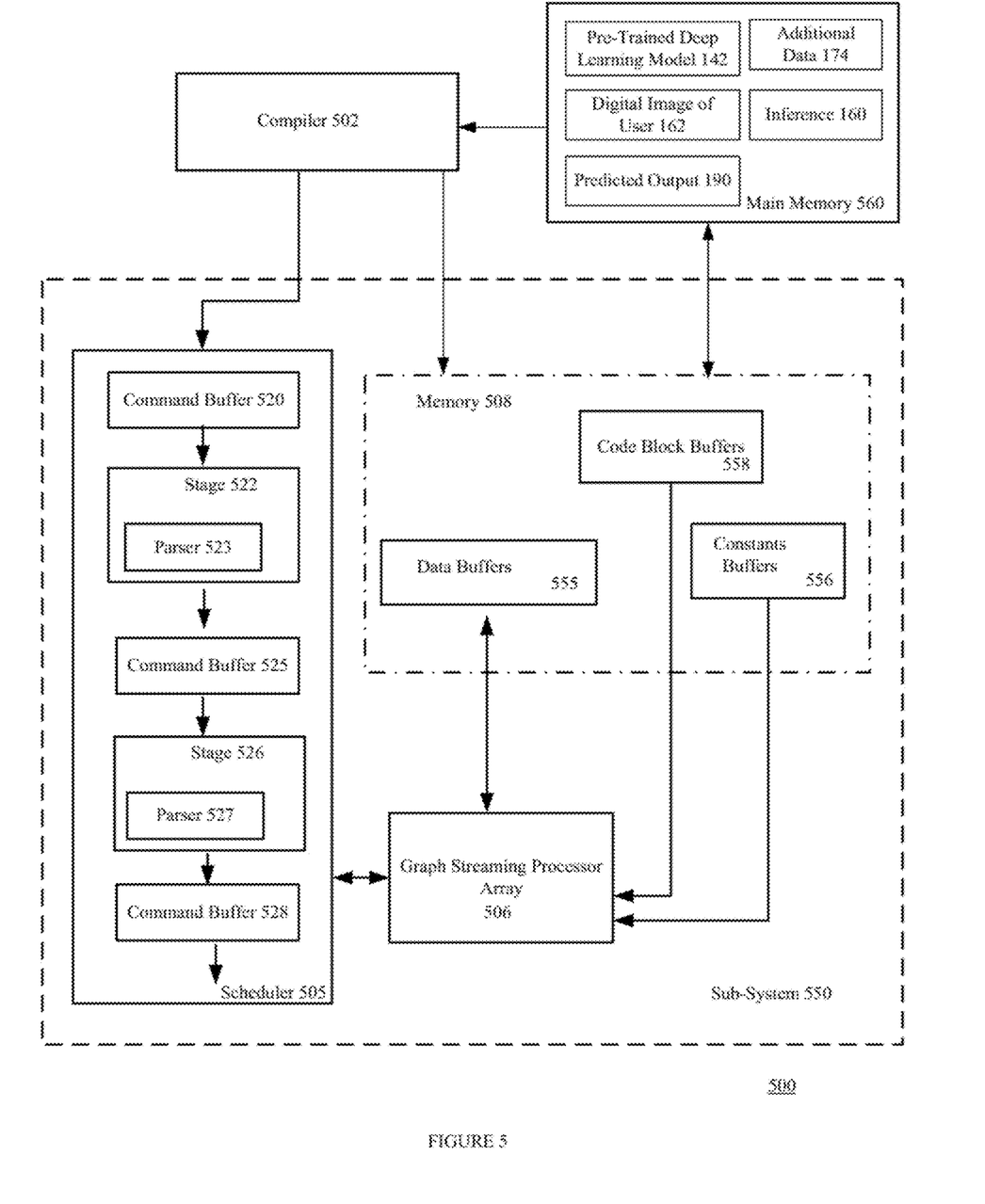
FIG. 5 shows a representation of a graph stream processing system according to an embodiment.

FIG. 5 describes an example edge device 150 comprising of a GSP system. In an embodiment, system 500 comprises of compiler 502, main memory 560 and sub-system 550. In a non-limiting embodiment, sub-system 550 includes scheduler 505, graph streaming processor (GSP) array 506, main memory 560 and memory 508.

Compiler 502 reads program code stored in main memory 560 and segments program code into code blocks to enable/optimize task parallelism of the processing. In an example the program code consists of processing a digital image of user 162 received by the system 500 for predicting one or more medical conditions through a pre-trained deep learning model 142. Model 142 is stored in main memory 560. The predicted output 190 processed by the GSP array 506 is stored in main memory 560 before displaying or stored in a database or sent to cloud storage or emailed to user. Memory 560 also stores digital image of user 162 and additional data 174 for execution of inference 160. Main memory 560 is generally a slower access large memory. For the described embodiments, block or code blocks refer to a section or portions of code grouped together. Grouping enables groups of statements to be treated as if they were one statement, and to restrict the scope of variables, procedures and functions declared in a block so that they do not conflict with variables having the same name used elsewhere in a program for different purposes. Flow constructs such as if and for loops cannot straddle code blocks. Each of these code-blocks is a set of instructions along with its inputs and outputs. The thread is a code-block which is scheduled for operation on the graph streaming processor (GSP) array 506. Each thread is a physical instance of a set of instructions (kernel/program/code-block) running on a set of data and producing output data. A kernel/program can be a code block of a larger program. For an embodiment, the compiler program splits up the program into code-blocks at points where the vector-ness/width of the code changes to enable/optimize task parallelism. The vector-ness/width indicates the degree of parallel processing.

For an embodiment, the scheduler 505 includes a plurality of stages 522, 526, wherein each of the stages (522, 526) include an interface to an input command buffer (520, 525) and input command buffer parser (523, 527) of the stages (522, 526). Each stage (522, 526) of the graph streaming processor system includes a physical piece of hardware in the scheduler which is responsible for scheduling the threads. The input command buffer parser 523, 527 generates the threads of the stage 522, 526 based upon commands of a command buffer 520, 525 located between the current stage and the previous stage. The command buffers have command written into them that provides parallel processing and trigger threads for later occurring stages.

The plurality of threads run on the graph streaming processor (GSP) array 506. For an embodiment, scheduling of a thread on the processors is based on availability of resources including a thread slot in a GSP 506, adequate space in the register file in the GSP and in the output command buffer for writing the commands produced by the executing instructions in the GSP.

For an embodiment, the threads running on the processors have instructions embedded by the compiler to spawn/create downstream threads. The execution of these instructions results in commands which are placed in the output command buffer of the stage which in turn becomes the input command buffer for the next (later) stage. The locations of the command buffers between the stages and the hardware implementation of the stages allows for substantial performance advantages over software implementations of the command buffers and schedulers (stages).

For an embodiment, a node is a code-block along with the inputs, outputs. A node can be split up into one or more threads with each thread running the same code-block but on different data and producing different data. More than one node can be included within a stage. A graph can provide a visual dependency relationship between the nodes. For an embodiment, a stage is a physical piece of hardware in the scheduler which is responsible for scheduling the threads corresponding to the node/s at a particular depth (relative timing of the nodes) in the graph. The stage includes an input command buffer parser. The node generates threads based on the commands in the command buffer.

Scheduler 505, schedules execution of the code blocks in one or more processors of the graph streaming processor array (GSP) 506. Scheduler 505 is coupled to the compiler, graph streaming processor array 506 and memory 508. For an embodiment, the scheduler 505 includes a plurality of stages and a plurality of command buffers located between each of the plurality of stages, wherein each stage includes physical hardware operative to schedule each of the threads, including an input command buffer parser operative to interpret commands within a corresponding input command buffer and generate the plurality of threads. In an embodiment a portion of scheduler 505 is implemented in hardware.

In a non-limiting example, memory 508 comprises a plurality of data buffers 555, command buffers 520, constants buffers 516 and code block buffers 518. Input command buffers 520, 525 store the index pointing to the data buffers 555. Index to the first input command buffer (520) connected to the compiler is provided by the compiler, subsequent indices are written by the graph streaming processor array. Stage 522 reads the command buffers 520 and schedules a thread in the graph streaming processor array 506 to execute instructions. The index to the data for execution of code by the processor array 506 is stored in command buffers 52. In some embodiments, command buffers 520 and 525 can also store pointer to code block buffers 518. Memory 508 may represent any suitable or desired information storage medium. Memory 508 may be coupled with processing array 506.

Data buffers 555, comprises of a plurality of buffers to store data for processing or for storing the results of processing. Data buffers 555 communicate with the graph streaming processor array 506. The index to the data buffer 555 is stored in the command buffer 520, 525. Code block buffer 518 stores the code blocks for execution by the processor array 506. In an embodiment, data buffers and command buffers are First in First out (FIFO) buffers, DRAM, MRAM or SRAM. Compiler 502 partitions the code and writes the code blocks in the code block buffer 518. The code block buffer 518 is read by the processor array 506 for execution. Compiler 502 stores constants required for code blocks in constants buffers 516. Processor array 506 reads the constants buffer 516 when required for execution of the code block. In some embodiments, constants buffer 516 is written by compiler 502 and read by GSP array 506.

While certain example techniques have been described and shown herein using various methods or systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter is not limited to examples disclosed, but that such claimed subject matter may also include all implementations falling within the scope of the appended claims, and equivalents thereof.

What is claimed:

1. A data processing method comprising:
   receiving a digital description of at least a symptom of one or more medical conditions in a first format;
   performing, using a plurality of GSP (Graph Stream Processors), an (AI (artificial intelligence) based) initial prediction of the one or more medical conditions by processing the digital description through a pre-trained deep learning model to generate a probability of the one or more medical conditions comprising of Covid-19;
   adjusting, using the plurality of GSP, the probability of the one or more medical conditions,
   identifying, using the plurality of GSP, a location in the description of the one or more medical conditions, and
   forecasting, using the plurality of GSP, a rate of spread of the one or more medical conditions and a spread of the one or more medical conditions over time based on a plurality of digital descriptions and additional medical data.

2. The method of claim 1, wherein receiving the digital description of at least the symptom of the one or more medical conditions in the first format comprises receiving a digital image of at least portion of a user.

3. The method of claim 2, further comprising pre-processing the digital image by removing noise, aligning, and correcting luminance of the digital image.

4. The method of claim 2, wherein a type of the digital image comprises any one of X-Ray, CT-Scan, and non-medical image.

5. The method of claim 3, wherein forecasting a rate of spread of the one or more medical conditions and a spread of the one or more medical conditions over time based on a plurality of digital descriptions and additional medical data comprises:
   generating an initial prediction, wherein the initial prediction comprises the probability of the one or more medical conditions by processing the pre-processed image through pre-trained weights of the pre-trained deep learning model; and
   predicting an output based on the initial prediction and further processing through the pre-trained deep learning model, where in the predicting includes,
   modifying the probability of the one or more medical conditions by labelling the preprocessed image from the one or more medical conditions and computing the probability of the one or more medical conditions; and
   identifying at least a location in the digital image effected by the one or more medical conditions, wherein the identifying includes generating a plurality of anchor boxes and estimating at least one final anchor box.

6. The method of claim 5, wherein the predicting further comprises receiving a plurality of digital images over a period of time and forecasting a rate of spread of the one or more medical conditions and spread of the one or more medical conditions over time based on additional medical data.

7. The method of claim 5, further comprising generating the pre-trained deep learning model comprising generating a floating-point model utilizing a plurality of data samples and compacting the floating-point model.

8. The method of claim 5, further comprising generating the pre-trained deep learning model comprising generating a floating-point model utilizing a plurality of data samples and quantizing the floating-point model to generate a mixed precision quantized model.

9. The method of claim 7, further comprising receiving a plurality of training data samples of a second medical condition, updating the floating-point model utilizing the plurality of training data samples of the second medical condition, and distilling the floating point model to update the pre-trained deep learning model.

10. The method of claim 7, further comprising receiving a plurality of new data samples, updating the floating-point model utilizing the plurality of new data samples, and distilling the floating point model to update the pre-trained deep learning model.

11. The method of claim 7, wherein the plurality of data samples comprises positive data samples and negative data samples, wherein the positive data samples comprises a plurality of data samples of a first type, and negative samples comprises a plurality of data samples in other type, wherein the plurality of data samples of the first type are used to generate the pre-trained deep learning model and negative samples are discarded.

12. The method of claim 11, further comprising labelling the positive samples with the one or more medical conditions, aligning images of the positive data samples and data balancing the plurality of data samples.

13. The method of claim 11, further comprising dividing the balanced data samples into training data samples for generating the pre-trained deep learning model, test data samples for testing the pre-trained deep learning model and validation data samples for validation of the pre-trained deep learning model.

14. The method of claim 13, further comprising the validating the pre-trained deep learning model by processing the validation data samples through the pre-trained deep learning model and comparing the predicted output with the positive samples.

15. The method of claim 13, further comprising, utilizing test data samples to test for system randomness.

16. The method of claim 1, further comprising generating the pre-trained deep learning model, where in the generating includes:
   pre-processing a plurality of training data samples to reduce noise, adjust illumination and image alignment to generate pre-processed training data samples;
   extracting textural features from the pre-processed training data samples;
   generating a map of the textual features; and
   processing through a decision network to train the pre-trained deep learning model to the predict the output.

17. A graph stream processing system, comprising:
an inference module operative to execute instructions on a plurality of graph streaming processors (GSP) to process a digital image associated with a patient, generating an initial prediction utilizing pre-trained weights in a mixed precision deep learning model; and
a post-processing module operative to execute instructions on the GSP to:
 receive a digital description of at least a symptom of one or more medical conditions in a first format;
 perform an (AI based) initial prediction of the one or more medical conditions by processing the digital description through a pre-trained deep learning model to generate a probability of the one or more medical conditions comprising of Covid-19;
 adjust the probability of the one or more medical conditions,
 identify a location in the description of the one or more medical conditions, and
 forecast a rate of spread of the one or more medical conditions and a spread of the one or more medical conditions over time based on a plurality of digital descriptions and additional medical data.

18. The system of claim 17, wherein receiving the digital description of at least the symptom of the one or more medical conditions in the first format comprises receiving a digital image of at least portion of a user.

19. The system of claim 18, wherein the post-processing module is further operative to execute instructions on the GSP to pre-process the digital image by removing noise, aligning, and correcting luminance of the digital image.

20. The system of claim 19, wherein forecasting a rate of spread of the one or more medical conditions and a spread of the one or more medical conditions over time based on a plurality of digital descriptions and additional medical data comprises:
 generating an initial prediction, wherein the initial prediction comprises the probability of the one or more medical conditions by processing the pre-processed image through pre-trained weights of the pre-trained deep learning model; and
 predicting an output based on the initial prediction and further processing through the pre-trained deep learning model, where in the predicting includes,
 modifying the probability of the one or more medical conditions by labelling the preprocessed image from the one or more medical conditions and computing the probability of the one or more medical conditions; and
 identifying at least a location in the digital image effected by the one or more medical conditions, wherein the identifying includes generating a plurality of anchor boxes and estimating at least one final anchor box.

* * * * *